United States Patent [19]
Low et al.

[11] Patent Number: 5,115,196
[45] Date of Patent: May 19, 1992

[54] GIRTH WELD DETECTION SYSTEM FOR PIPELINE SURVEY PIG

[75] Inventors: Stanley T. Low, Tucson, Ariz.; Pedro F. Lara, Dallas, Tex.; David L. Foreman, Tucson, Ariz.; Steven G. Petermann, Plano, Tex.

[73] Assignee: Atlantic Richfield Company, Los Angeles, Calif.

[21] Appl. No.: 201,009

[22] Filed: Jun. 1, 1988

[51] Int. Cl.$^5$ .................... G01N 27/72; G01N 27/82; G01R 33/12
[52] U.S. Cl. ..................................... 324/220; 324/262
[58] Field of Search ............... 324/219, 220, 221, 226, 324/262; 346/33 P, 107 W; 354/63; 15/104.05; 104/138.1, 138.2

[56] References Cited

U.S. PATENT DOCUMENTS

| | | | |
|---|---|---|---|
| 3,754,275 | 8/1973 | Carter et al. | 324/220 |
| 4,598,250 | 7/1986 | Lorenzi et al. | 324/220 |

FOREIGN PATENT DOCUMENTS

| | | | |
|---|---|---|---|
| 1202368 | 3/1986 | Canada | 324/220 |
| 2704838 | 8/1978 | Fed. Rep. of Germany | 324/238 |

Primary Examiner—Walter E. Snow
Attorney, Agent, or Firm—Michael E. Martin

[57] ABSTRACT

A weld detection system for a pipeline survey pig includes a plurality of weld sensor units mounted spaced apart circumferentially on fore and aft pig support members and arranged in close proximity to the pipe wall. The sensor units comprise permanent magnet members for generating a magnetic flux field around a wire coil which is modified upon passing a girth weld or other magnetic anomaly in the pipe to produce a voltage signal which is conditioned by an amplifier and filter circuit to a signal suitable for input to a digital activation circuit. The digital activation circuit receives conditioned signals from opposed pairs of sensor units on the support members to distinguish transverse girth welds from spiral or longitudinal welds. The digital activation circuit includes circuit elements for timing the sensor output signals of the fore and aft detector arrays for measuring the velocity of the survey pig through the pipe. Each sensor unit comprises a high intensity permanent magnet disposed on a compact wire coil and support spool and arranged so that the flux field extends through the pipe wall during normal operation of the system. The output signal from the sensor units is capable of being conditioned for use in determining changes in pipe wall thickness and changes in axial strain on a pipe section of known length.

5 Claims, 6 Drawing Sheets

GIRTH WELD DETECTION SYSTEM FOR PIPELINE SURVEY PIG

BACKGROUND OF THE INVENTION

1. Field of the Invention

The present invention pertains to a magnetic sensor and associated circuit arrangement for a pipeline survey pig for detecting girth welds and other magnetic anomalies in fluid transmission pipelines.

2. Background

The development of pipeline survey pigs for accurate determination of the location or change in location of fluid transmission pipelines has become increasingly important with the continuing growth of pipeline networks and the desire to minimize the risk of pipeline failure and the consequent economic and environmental damage. One major improvement in pipeline survey pigs is disclosed and claimed in U.S. Pat. No. 4,747,317, issued May 31, 1988 in the name of Pedro F. Lara and assigned to the assignee of the present invention. The survey pig disclosed in the above identified patent application utilizes an inertial sensing unit to determine the course of a pipeline through which the pig is traversed and/or to determine any change in course of the pipeline from a previous survey. The survey pig described in the above identified application would also benefit from an accurate velocity and longitudinal position determining system, particularly in pipelines which have known position markers which may be sensed by a magnetic circuit.

For example, certain fluid transmission pipelines have well documented locations and spacings of circumferential girth welds which are used to join the sections of pipe together. Accordingly, a detection system which can accurately determine when a girth weld is being passed by the survey pig can utilize the location detection signal to accurately measure survey pig velocity, longitudinal position in the pipe and, as determined in pursuing the present invention, certain characteristics of the pipe wall and whether or not any axial strain is being encountered by the pipe which will result in elongation or compression of the pipe sections.

Certain problems in the art of pipeline survey pigs and associated detection apparatus have been required to be overcome in pursuing the present invention. For example, it has been determined that it is highly desirable to provide a magnetic sensing device which will detect a magnetic anomaly caused by a pipeline girth weld, which device can be located in proximity to the wall surface of the pipe, can provide a well defined electrical signal and which physically occupies a minimum amount of space. One preferred type of pipeline survey pig utilizes a generally cylindrical housing which is supported in the pipeline by a plurality of axially spaced apart generally annular resilient cup-like support members. These cup members are adapted to support the pig body in the pipe while providing for propulsion of the pig through the pipe by the force of fluid acting on one or more of the cup members. Accordingly, it has been considered desirable to provide a magnetic field sensing circuit which may be mounted in proximity to the pipe wall on one or more of the resilient cup members or similar structure and which can provide an electrical signal which may be modified to become a suitable digital input signal to a microprocessor based control and recording system for the survey pig.

Another problem associated with developing a suitable girth weld detection system for pipeline survey pigs relates to providing a system which will accurately determine the presence of a girth weld but which will avoid giving false readings which may result from spiral or longitudinal welds as well as magnetic anomalies caused by pipeline repairs, various devices interposed in the pipeline, such as valves, and other structures in the vicinity of the pipe which might generate a sufficiently intense magnetic field to provide a false signal from the girth weld detection circuit. The problems recognized in the art of magnetic weld detector systems and the advantages sought for such a system as described herein have been provided by the present invention. Somewhat related devices and systems are disclosed in U.S. Pat. No. 3,238,448 to Wood et al.; U.S. Pat. No. 3,449,662 to Wood; U.S. Pat. No. 3,483,466 to Crouch et al.; U.S. Pat. No. 4,372,658 to O'Connor et al.; U.S. Pat. No. 4,447,777 to Sharp et al.; U.S. Pat. No. 4,598,250 to Lorenzi et al.; U.S. Pat. No. 4,649,343 to Birchak et al. and U.S. Pat. No. 4,675,604 to Moyer et al.

SUMMARY OF THE INVENTION

The present invention provides a girth weld detection system for use in pipeline survey pigs to determine the location of girth welds and to detect other magnetic anomalies as well as to provide electrical signals suitable for measuring survey pig velocity or position in a fluid transmission pipeline.

In accordance with one aspect of the present invention, one or more magnetic flux sensor units are provided on a pipeline survey pig which provide an improved electrical signal which may be easily distinguished from spurious signals and may be easily converted to a signal suitable for digital processing using improved signal conditioning circuits.

In accordance with another aspect of the present invention, a girth weld detection system is provided which distinguishes circumferential, generally transverse girth welds from spiral or longitudinal welds or other magnetic anomalies which may be encountered in a fluid transmission pipeline. In this regard, a plurality of unique magnetic anomaly sensor units are provided on each of at least two spaced apart support members for a pipeline survey pig and arranged in substantially transverse planes with respect to the longitudinal axis of the survey pig for generating electrical signals when passing a magnetic anomaly such as girth welds or the like.

The weld detection system includes a unique circuit for receiving and conditioning the signals generated by each of the weld detectors to distinguish a girth weld from other magnetic anomalies sensed by the respective detector units so that a signal is provided for further treatment and recording which is related only to a girth weld as opposed to signals representing spiral or longitudinal pipe welds, for example.

The present invention still further provides an improved magnetic sensor unit which may be placed in close proximity to the wall of a pipeline and which is particularly sensitive to magnetic anomalies caused by girth welds as well as other pipe conditions. The improved sensor units generate an easily measured, high resolution electrical signal, thanks to the particular construction of the sensor unit itself.

Still further in accordance with the present invention, a magnetic flux responsive sensor unit and associated circuit are provided which may be utilized to measure axial strain on pipe sections of known length and may be utilized to generate signals related to defects in the wall structure of a pipeline or the like.

The above-described advantages and superior features of the present invention together with other important aspects thereof will be further appreciated by those skilled in the art upon reading the detailed description which follows in conjunction with the drawing.

BRIEF DESCRIPTION OF THE DRAWING

FIGS. 5A and 5B comprise is a schematic diagram of a digital circuit for generating signals related to the detection of girth welds and other magnetic anomalies in a fluid transmission pipeline or the like.

DESCRIPTION OF A PREFERRED EMBODIMENT

In the description which follows, like parts are marked throughout the specification and drawing with the same reference numerals, respectively. The drawing figures are not necessarily to scale and certain elements are shown in schematic form in the interest of clarity and conciseness.

Figure 1:
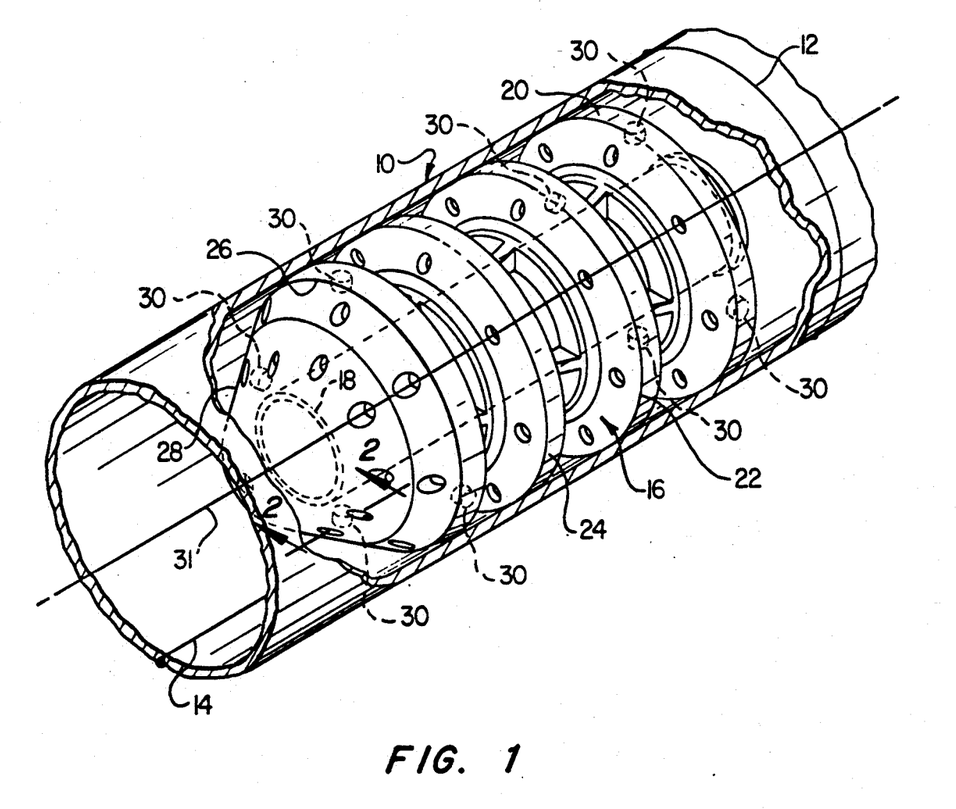
FIG. 1 is a perspective view of a pipeline survey pig including the detection system of the present invention.

Referring to FIG. 1, there is illustrated a section of a fluid transmission pipeline, generally designated by the numeral 10, including a generally transverse girth weld 12 commonly used to join predetermined lengths of pipe together end to end. Certain types of pipe may also include longitudinal welds such as the weld 14, illustrated, or spiral welds, not shown. The girth weld detection system of the present invention is advantageously used in conjunction with a pipeline survey apparatus or "pig", generally designated by the numeral 16. The survey pig 16 may be of the type generally described in the above-mentioned U.S. Pat. No. 4,747,317 and includes a body member 18 which houses certain survey instruments, not shown, and which is supported for traversal through the pipeline 10 on spaced apart, generally cylindrical cup-like support members 20, 22, 24 and 26. A resilient nose member 28 is also preferably provided for the survey pig 16. The cup members 20, 22, 24 and 26 are of similar construction and are preferably formed of a molded polyurethane material which has sufficient resiliency to permit the outer peripheral surfaces of the cup members to engage the wall of the pipe but to be deflected slightly radially inwardly as the survey pig traverses through the pipe and moves over the girth welds 12, for example. The survey pig 1 6 is typically propelled through the pipeline by pumping fluid through the pipeline behind the pig in a conventional and well known manner.

In accordance with the present invention the survey pig.16 is provided with a plurality of weld detector or sensor units 30 which are preferably mounted spaced apart in a common transverse plane and around the periphery of the forward cup member 26 and the aft cup member 20, respectively. In a preferred arrangement of the weld sensor units or devices 30, four units 30 are provided spaced apart 90° from each other with respect to the longitudinal central axis 31 of the survey pig on both the forward cup member 26 and the aft cup member 20. Diametrically opposed pairs of the sensor units 30 are suitably electrically connected in a circuit to be described herein such that when a substantially transverse girth weld, such as the weld 12, is encountered by the survey pig, an electrical signal is generated as each unit 30 passes the weld. If the weld is a substantially transverse girth weld, that is lying in a plane normal to the axis 31, the sensor units 30 of each pair will generate a signal substantially simultaneously as that pair of units passes the weld. Signals generated by the associated pairs of sensor units 30 may thus be handled by suitable circuitry to be described herein to determine if, in fact, a girth weld has been passed or some other magnetic anomaly in the pipeline is being encountered.

Figure 2:
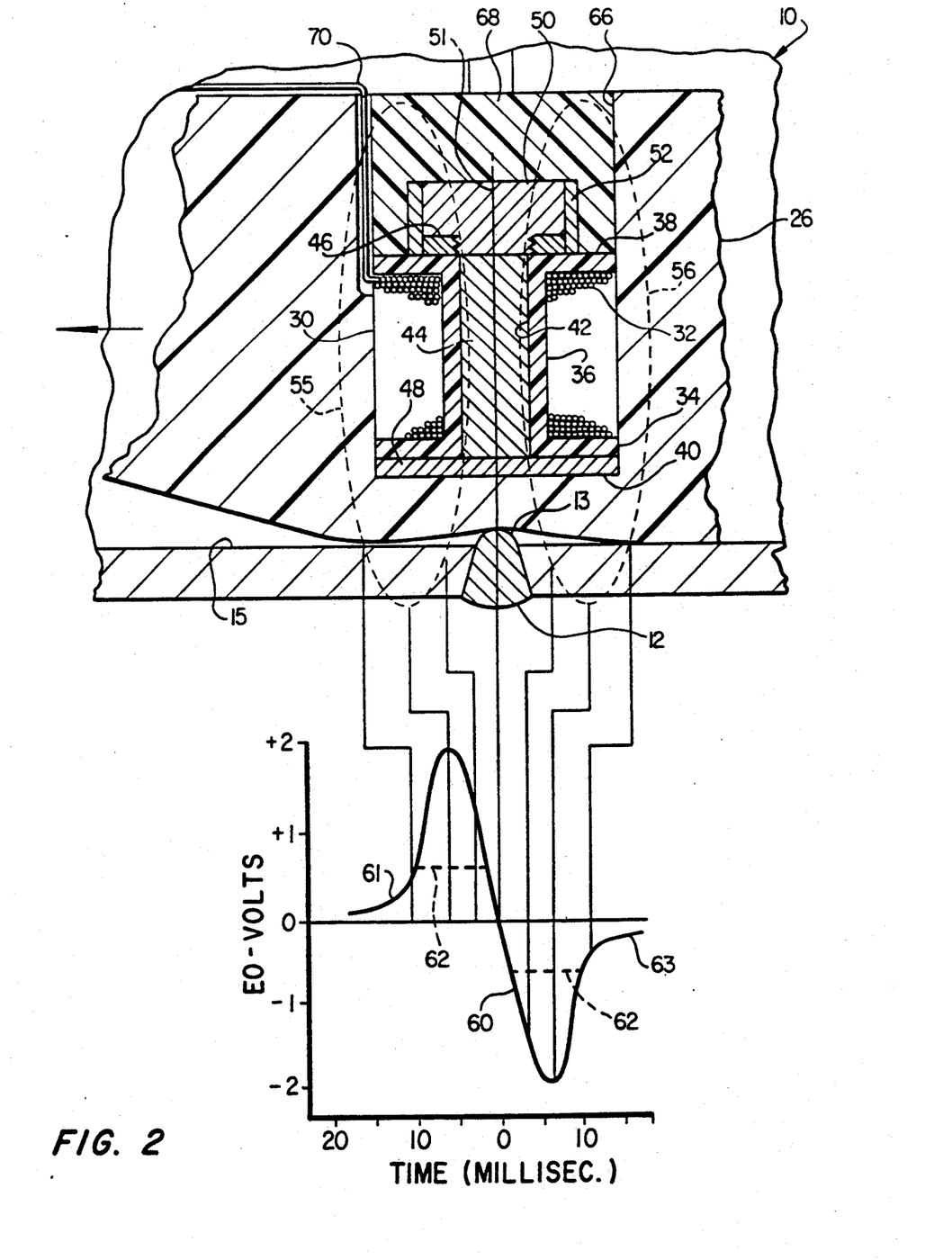
FIG. 2 is a transverse section view of one of the weld sensor units shown passing a pipeline girth weld and including a schematic diagram indicating the electrical signal generated by the sensor unit.

Referring now to FIG. 2, one embodiment of a sensor unit 30 supported by the cup member 26 is illustrated in detail. Each of the sensor units 30 comprises a high inductance wire coil 32 wound around a nonmagnetic spool or bobbin member 34. The spool member 34 is preferably formed of brass, aluminum or a plastic material, as shown, and is characterized by a generally cylindrical hollow hub 36 and opposed flange members 38 and 40. The hub 36 includes a hollow interior cavity 42 in which a soft iron core member 44 is disposed and retained therein by opposed nonmagnetic end plates 46 and 48. A permanent magnet 50 is supported on the end plate 46 coaxial with the longitudinal central axis 51 of the spool 34 and is surrounded by a cylindrical Mumetal shield member 52. The arrangement of the iron core 44 with respect to the magnet 50 and the provision of the Mumetal shield 52 provides for generally uniform magnetic flux paths, as indicated by the representative flux lines 55 and 56, which are disposed around and symmetrical with respect to the axis 51. Alternatively, if the overall length of the sensor unit requires reduction the member 44 could comprise a magnet and the magnet 50 and shield 52 could be deleted.

As indicated in FIG. 2, the sensor unit 30 is arranged to have its central longitudinal flux field axis 51 substantially normal to the axis 31 of the pipe and the pig 16 so that upon passing a girth weld 12 a magnetic anomaly caused by the girth weld induces a voltage in the coil 32 having a characteristic generally indicated by the schematic diagram in FIG. 2 and indicated by the line 60. The voltage characteristic (EO) illustrated in FIG. 2 is measured across the coil 32 when the sensor unit 30 is moved at a predetermined velocity from right to left, viewing FIG. 2, past a girth weld 12. The sensor coil voltage (EO) can be accounted for in accordance with known electromagnetic induction laws. The induced voltage characteristic signal 60 is typical for detecting a conventional pipeline girth weld with the sensor unit 30. However, on changing the weld shape such as when the inward protruding portion 13 is ground flush with the pipe wall, a voltage characteristic following the line 62 is induced in the coil as the sensor unit moves past the weld. Moreover, the sharp positive to negative voltage transition characteristic illustrated in FIG. 2 has been determined to be a particularly ideal type of signal for processing in an electronic circuit for digital data processing purposes as will be evident to those skilled in the art from the further description of such a circuit hereinbelow. The particular values of voltage versus time indicated for the diagram in FIG. 2 and the approximate waveform have been observed with a sensor unit 30 having a coil 32 formed of approximately 22,500 turns of No. 37 enameled, single strand copper magnet wire wound on the spool 34 having a nominal section thickness of approximately 0.062 inches and being formed of a molded plastic material such as Lexan. A steel core having approximately 0.50 inches diameter by 1.38 inches length is disposed in the space 42. A permanent magnetic capable of generating a flux density of approximately $10^4$ gauss is used to form the magnet 50. The voltage signal characteristics indicated in FIG. 2 can be generated with a sensor unit 30 as described above moving at a velocity of about 10.0 feet per second at a distance of approximately 0.75 inches from the weld 12 and with a pipe wall thickness of approximately 0.50 inches. As indicated hereinbefore, the magnet 50 may be modified to occupy the space 42 in place of the core 44.

As illustrated in FIG. 2, the sensor unit 30 is suitably mounted in a cavity 66 formed in the cup member 26 and is typical of the mounting of all of the sensor units 30 on both members 20 and 26. Suitable retaining means such as a plug 68 secures the sensor unit 30 within the cavity 66 and sealed from intrusion of pipeline fluids. The ends of the conductor wire making up the coil 32 are suitably cased in insulation and comprise a so-called twisted pair conductor, generally designated by the numeral 70, which is suitably trained along the support member 26 and to suitable circuit means disposed within the interior of the body 18, not shown in FIG. 2. Accordingly, by utilizing magnetic induction principles in a uniquely constructed sensor unit, means are provided for generating an electrical signal, upon sensing a magnetic anomaly such as a girth weld in a steel pipe, which does not require any external electrical power to generate a signal of sufficient quality as to be easily conditioned for input to a digital logic circuit so that the signals generated by the sensor units 30 will differentiate transverse girth welds from spiral welds, longitudinal welds or other magnetic anomalies encountered by a survey pig moving through a section of pipeline.

Figure 3:
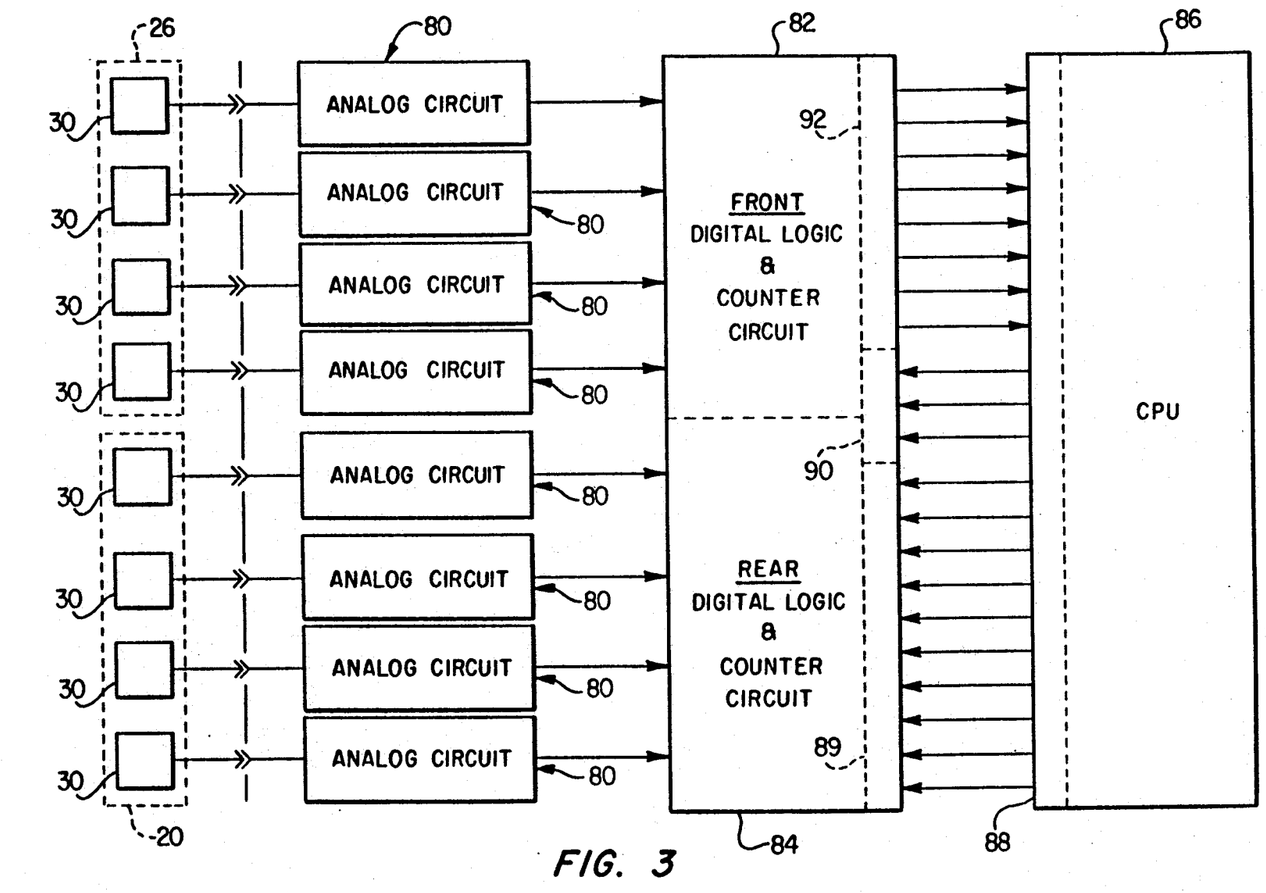
FIG. 3 is a block diagram showing the main elements of the detection system of the present invention.

Referring briefly to FIG. 3, there is illustrated a functional block diagram showing the respective sensor units 30 which are associated with the forward support cup member 26 and the sensor units 30 which are associated with the rear or aft support member 20. Each sensor unit 30 provides an output signal which is transmitted to a separate signal conditioning circuit, generally designated by the numeral 80. A circuit 80 is provided for each sensor unit 30 and is adapted to provide an output signal to a digital logic and counter circuit which is operable to provide suitable output signals to a central processing unit. As illustrated, each circuit 80 for the sensor units disposed on the forward cup member 26 provides an output signal to a digital logic and counter circuit 82 and each sensor unit 30 disposed on the aft cup member 20 provides an output signal to a digital logic and counter circuit 84. The circuits 82 and 84 are suitably connected to a central processing unit 86 having an address/control and data bus 88 suitably connected to an appropriate address bus 89, a control bus 90 and a data bus 92.

Figure 4:
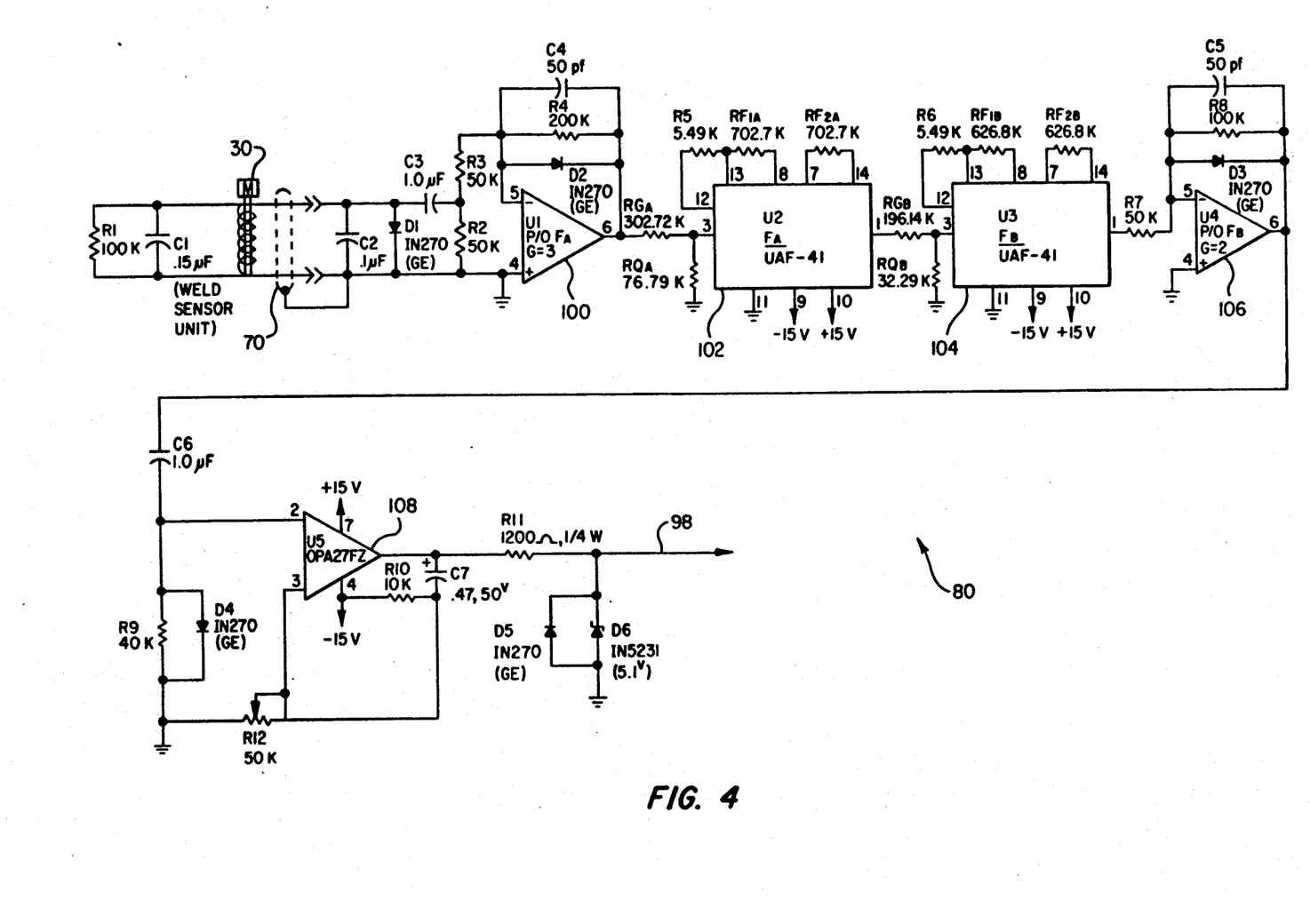
FIG. 4 is a schematic diagram of an analog circuit for modifying the characteristics of the electrical signal generated by the weld sensor unit.

Referring now to FIG. 4, by way of example, one of the signal conditioning circuits 80 is illustrated in detail. The circuit 80 is adapted to provide a signal suitable for digital circuit activation. In particular, it is desired to provide a signal imposed on conductor 98 having a steep rise and fall pulse characteristic of approximately 5.0 volts maximum amplitude. Preferably the pulse width is adjustable from about 4.7 to about 28.0 milliseconds and the leading edge of the pulse should represent the point in time that the sensor unit 30 is centered over a girth weld 12, for example. In the circuit illustrated in FIG. 4, the weld sensor unit 30 is indicated schematically and is in circuit with a resistor R1 and a capacitor C1 for tuning and impedance normalization. The signal from the sensor unit 30 is conducted by way of the twisted pair, shielded conductor 70 to the circuit 80 which is preferably suitably mounted within the body 18 of the survey pig.

The circuit 80 includes a passive differentiator/clipper circuit made up of capacitor C2, diode D1, capacitor C3 and resistor R2. The resultant signal from this circuit section is a negative going pulse in the range of about 0.25 to 2.5 volts based on an input signal range of about 0.5 to 5.0 volts peak to peak as indicated by the signal characteristic 61 through 63 illustrated in FIG. 2. The modified pulse signal is input to an inverting amplifier 100 having a gain set by resistors R3 and R4. The output of the amplifier 100 is primarily a positive pulse having a magnitude in the range of about 1.0 to 10.0 volts peak and a pulse width of approximately 15 milliseconds. This signal is imposed on a four pole Bessel low pass filter made up of circuit elements 102 and 104 with an approximate gain of 1.0 at all frequencies below 50 Hz. The filter response is set with the calculated selection of the resistors associated with the circuit elements 102 and 104 and, for the particular application of the sensor unit 30 in the survey pig 12, the filter results in a high reduction of signal response to signal frequencies above 50 Hz so as to reject high frequency noise and spurious signals.

The output signal at pin 1 of circuit element 104 is input to an inverting amplifier 106 preferably having a gain of 2.0 set by resistors R7 and R8 which produces a negative output pulse on the order of about −12.0 volts maximum. The positive portion of the output voltage signal is limited by diode D3 to approximately 0.3 volts. The signal output from amplifier 106 is input to a second passive differentiator/clipper circuit comprising capacitor C6, resistor R9 and diode D4 which produces a negative going pulse to an analog one shot multivibrator circuit 108 and the associated resistors and capacitors illustrated in the circuit diagram of FIG. 4.

As previously mentioned, the output signal on conductor 98 is controlled to be from between −0.3 to +5.1 volts as provided by the diodes D5 and D6 and the pulse width is adjustable from about 4.7 to 28 milliseconds by the variable resistor R12. Commercial designations and sources for the circuit elements 100, 102, 104, 106 and 108 are as follows:

| | | |
|---|---|---|
| 100 | ⎫ | UAF-41 Active Filter, Burr-Brown, Inc. |
| 102 | ⎭ | Tucson, AZ |
| 104 | ⎫ | UAF-41 Active Filter, Burr-Brown, Inc. |
| 106 | ⎭ | Tucson, AZ |
| 108 | } | OPA27 op.amp., Burr-Brown, Inc. |
| D1 through D5-IN270 diode, General Electric Company | | |
| D6-IN5231, Zener Diode, General Electric Company | | |

The numerals associated with each of the circuit elements 100, 102, 104, 106 and 108 at respective terminals thereof identify the actual pin numbers of these commercially available circuit elements.

Figure 5A:
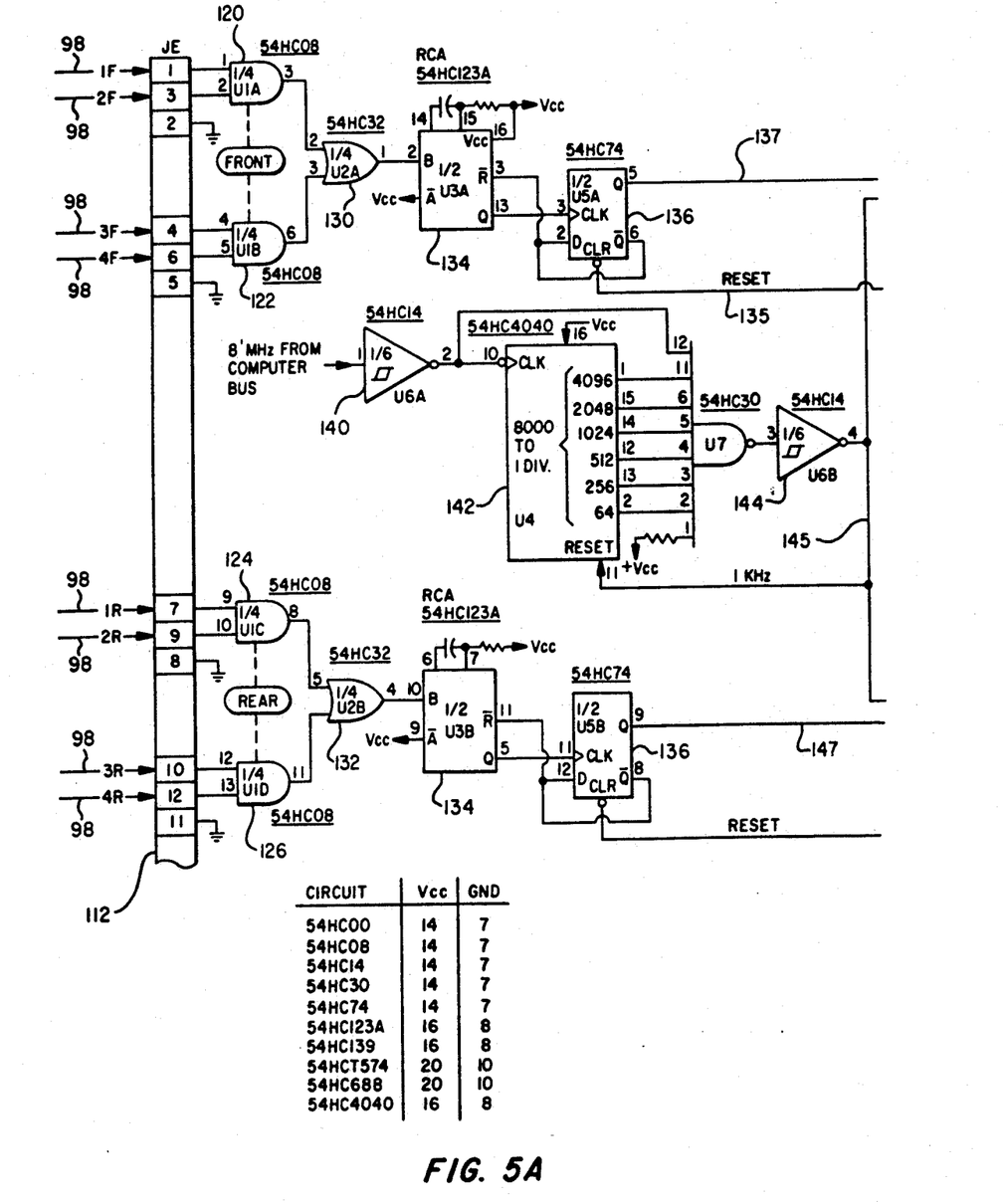
Figure 5B:
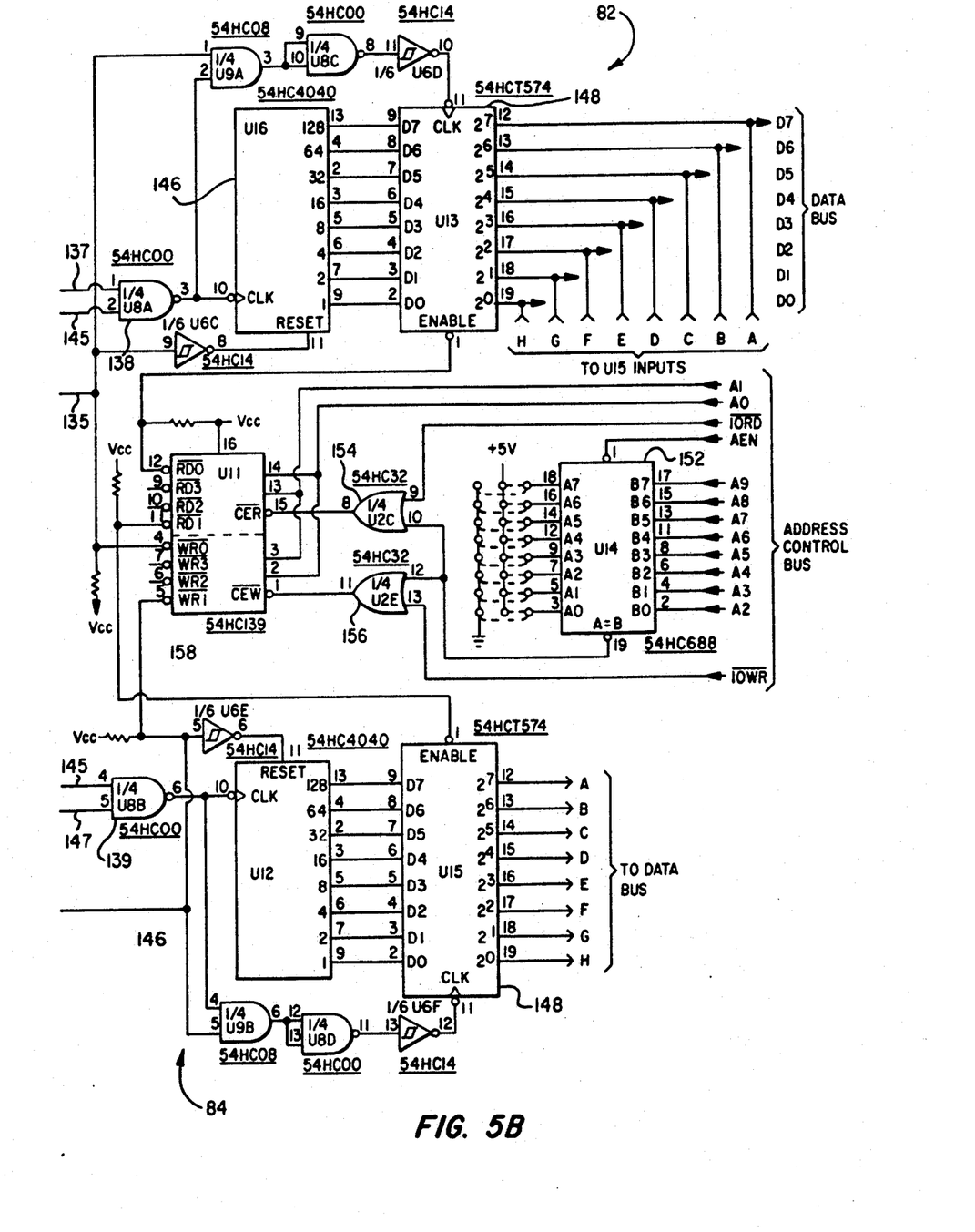

Referring now to FIGS. 5A and 5B, there is illustrated a circuit diagram comprising the detection system digital circuit for receiving the output signals from each of the circuits 80. FIG. 5B is a continuation of the circuit shown in FIG. 5A from the matching conductor lines indicated in both figures. The input signals to the digital circuits 82, 84 from the respective sensor units 30 are carried by conductors 98 to terminals indicated by the numerals 1F, 2F, 3F, 4F on terminal board 112 for the weld sensor units 30 on the cup member 26. The sensor units 30 associated with the cup member 20 have their respective analog circuit output signals transmitted through to terminal board 112 by way of terminals labeled 1R, 2R, 3R and 4R, respectively. Opposed pairs of the weld sensor units 30, that is pairs which are mounted substantially coplanar on the respective cup members about 180° apart with respect to the longitudinal axis 31 of the survey pig and in a plane normal to said axis, are paired for providing input signals to the respective AND gates 120, 122, 124 and 126, as indicated in FIG. 5.

Accordingly, when a pair of sensor units 30 on the support or cup member 26 provide a simultaneous output signal to their associated AND gates an output signal is provided to respective OR gates 130 and 132 as shown in FIG. 5. By providing two pairs of opposed sensor units 30 on both the front and rear support members 26 and 20, respectively, a redundancy in the girth weld detector sensing system is provided. As long as an electrically connected pair of sensor units 30 senses the presence of a weld at substantially the same time, indicating a girth weld, an output signal will be generated at the OR gates 130 and 132. However, if spiral or longitudinal welds are sensed by the weld sensor units 30, each opposed pair of sensor units will not generate an output signal at the same time. The one hundred percent redundancy of the girth weld sensing system provides for substantial reliability in the event of failure or malfunction of one of the sensor units 30 or its respective analog conditioning circuit 80.

The OR gate 130 will provide an output signal (a voltage "high" signal) when there is an output signal imposed on either or both of its input terminals from the AND gates 120 and/or 122. The output signal from OR gate 130 is input to a one shot multivibrator 134 on its terminal pin 2. This provides an output signal which is a relatively narrow width positive voltage pulse that is used to trigger a D-edge flip flop circuit 136 to provide an output signal on conductor 137 which is input to a NAND gate 138 until circuit 136 is reset via a signal on conductor 135.

The circuit illustrated in FIGS. 5A and 5B also receives an 8 MHz square wave clock signal imposed on an inverter buffer circuit 140 which produces an output signal to a countdown counter 142 to provide an output voltage at pin 4 of circuit 144 comprising a 1 KHz square wave signal. This one KHz square wave signal is input to the NAND gates 138 and 139 over conductor 145. The output signals from the gates 138 and 139 are input to respective binary ripple counter circuits 146 which are connected as illustrated. The NAND gate 139 receives a signal from the circuit associated with the sensor units 30 on the support member 20 via conductor 147.

Preferably the computer or CPU 86 shown in FIG. 3 is provided with a real time calendar clock function which monitors the current time of day during operation. In a preferred embodiment of the present invention, one parameter to be stored by the CPU 86 is the identification of the girth welds encountered by the sensor units 30 mounted on the cup member 26. Another parameter to be recorded is the velocity of the survey pig 16 as it proceeds through a fluid transmission pipeline. The CPU 86 is capable of calculating the average velocity by solving the equation wherein velocity is equal to the distance travelled divided by the interval of time. The distance between the cup members 20 and 26 is known and the time accumulated between weld interruptions is measured by the clock circuits 146 which are respectively connected to flip flop latches 148. As indicated in the diagram of FIGS. 5A and 5B, when a weld is sensed at NAND gate 138 the ripple counter 146 will begin counting as activated by the 1 KHz clock in one millisecond steps until interrupted by the CPU 86 at 200 millisecond intervals. The one millisecond counts that exist on the latch output lines $2^0$ through $2^7$ will be subtracted by the CPU 86 from the total time accumulated between weld interruptions to provide the time interval for calculating velocity.

Read and write control lines along with address lines are input to the circuits 152, 154, 156 and 158 from the CPU 86 and which provide control selection of either the front or rear weld sensor units output signals as well as the necessary address decoding. Accordingly, the number of welds encountered and the time of encounter of the weld as well as velocity of the survey pig 16 may be reliably obtained using the sensor units 30 and the circuits illustrated in FIGS. 4, 5A and 5B.

Referring again to FIG. 2, it has been observed in developing the present invention that variations in the residual DC voltage signal portions indicated by the numerals 61 and 63 appear to exist when the sensor units 30 are traversing the pipe between girth welds. As indicated previously, the circuits 80 are adapted to remove these component portions of the sensor output signal. However, it is indicated that the remnant signal indicated by the signal portions 61 and 63 ma be related to the thickness of the pipe wall or the physical condition of the pipe.

Still further in accordance with the present invention, it has been indicated that the significantly well defined amplitude and narrow pulse width of the signal generated by the sensor units 30 and conditioned by the circuits 80 provides a timing accuracy which may also be utilized to measure axial strain on pipe sections which have a known length or which have been previously measured by the survey pig 16. If sufficient accuracy of the velocity of the survey pig 16 can be ascertained as it moves through a section of known length as by using an accurate inertial sensing unit as described in U.S. Pat. No. 4,747,317 and if a forty foot section length is previously known to within an accuracy of about 1.0 inches it is indicated that the longitudinal axial strain may be measured to an accuracy of about 1% with the system of the present invention.

The operation of the system described herein is believed to be readily understandable to those of ordinary skill in the art from the foregoing description taken in conjunction with the drawing figures. Moreover, those skilled in the art will recognize that various substitutions and modifications may be made to the particular embodiment described without departing from the scope and spirit of the invention as recited in the appended claims.

What is claimed is:

1. A method for determining the change in length of a section of fluid transmission pipeline comprising the steps of:

providing a pipeline survey pig including spaced apart support members for supporting said survey pig in said pipeline and for traversal therethrough, means for sensing a change in the velocity of said pig when traversing said section of pipeline, a first sensor unit mounted on one of said support members and a second sensor unit mounted on the other of said support members and in proximity to the wall surface of said pipeline, each of said sensor units including means for generating a magnetic flux field which is interruptible upon passing in proximity to a first magnetic anomaly associated with said section of said pipeline, each of said sensor units being adapted to provide an output signal upon sensing said first magnetic anomaly;

providing circuit means for receiving output signals from each of said sensor units and for recording the elapsed time between one of said sensor units sensing said first magnetic anomaly and the other of said sensor units sensing said first magnetic anomaly;

traversing said pig through said pipeline and monitoring said sensor units to determine when an output signal is received from a sensor unit, respectively;

measuring the elapsed time between output signals from each of said sensor units upon sensing said first magnetic anomaly to determine the velocity of said survey pig through said pipeline;

measuring any change in said velocity of said pig while traversing said section of pipeline;

monitoring said sensor units to determine when an output signal is received from a selected one of said sensor units indicating the passage of a second magnetic anomaly associated with said section of pipeline; and comparing the elapsed time between the sensing of said first magnetic anomaly and said second magnetic anomaly by said selected sensor unit with the velocity of said survey pig through said pipeline to determine the distance between said first and second magnetic anomalies.

2. In a pipeline survey pig adapted to transverse a section of generally cylindrical fluid transmission pipeline made up of pipe sections which are welded end to end with generally transverse girth welds, said survey pig including spaced apart support members for supporting said survey pig for traversal through said pipeline, a girth weld detection system characterized by:

a first girth weld sensor unit disposed on one of said support members in relatively close proximity to an interior wall surface of said pipeline, said first sensor unit including means for generating a magnetic flux field which is interruptible by a girth weld as said first sensor unit passes said girth weld while said pig is traversing said pipe, said first sensor unit including means for generating an electrical sensor output signal in response to interruption of said magnetic fluid field;

a second sensor unit mounted on said one support member spaced apart circumferentially from said first sensor unit;

circuit means operably connected to said first and second sensor units for receiving sensor output signals and for generating signals related to said sensor output signals, respectively;

circuit means for receiving output signals from said sensor units, respectively, upon sensing an interruption of their respective magnetic flux fields and for generating a circuit output signal related to said sensor units sensing only a girth weld of said pipe;

first and second sensor units mounted on said other support member and including circuit means associated therewith for generating a signal in response to output signals from said sensor units on said other support member when said sensor units on said other support member pass a girth weld; and circuit means for timing the generation of signals related to said sensor units on said one support member passing said girth weld and said sensor units on said other support member passing said girth weld for determining the velocity of said pig in said pipe.

3. In a pipeline survey pig adapted to traverse a section of generally cylindrical fluid transmission pipeline made up of pipe sections which are welded end to end with generally transverse girth welds, said survey pig including spaced apart support members for supporting said survey pig for traversal through said pipeline, a girth weld detection system comprising:

a first pair of girth weld sensor units disposed on said pig spaced apart from each other and in relatively close proximity to an interior wall surface of said pipeline, each of said sensor units including means for generating a magnetic fluid field which is interruptible by a girth weld as said sensor units pass said girth weld while said pig is traversing said pipeline, each of said sensor units including means for generating an electrical output signal in response to interruption of said magnetic flux field, respectively;

electrical circuit means operably connected to said sensor units, respectively, for receiving output signals from each of said sensor units and for generating a pulse signal related to said output signal and indicating when said first pair of sensor units has passed said girth weld;

circuit means for receiving the pulse signals from each of said sensor units and for comparing said pulse signals to determine if said first pair of sensor units has passed a girth weld in said pipeline;

a second pair of sensor units disposed on said pig and spaced apart with respect to the longitudinal central axis of said pig from said first pair of sensor units, said sensor units of said second pair being spaced apart one from the other and disposed in proximity to said interior wall surface of said pipeline for generating electrical output signals in response to interruption of magnetic fluid fields generated by said sensor units of said second pair; and circuit means electrically connected to receive signals related to the output signals of said first pair of sensor units and said second pair of sensor units for providing a signal indicating the velocity of said pig through said pipeline.

4. A method for sensing transverse girth welds in a fluid transmission pipeline using a pipeline survey pig traversing the interior of said pipeline, said method comprising the steps of:

providing a pipeline survey pig including spaced apart support members for supporting said survey pig in said pipeline for traversal therethrough;

providing a first pair of sensor units mounted on one of said support members spaced apart one from the other and in proximity to the wall surface of said pipeline;

providing a second pair of sensor units on another of said support members and spaced apart from each other on said other support member;

each of said sensor units including means for generating a magnetic fluid field which is interruptible upon passing in proximity to a magnetic anomaly associated with the wall of said pipeline, each of said sensor units being adapted to provide an output signal upon sensing said magnetic anomaly;

providing circuit means for receiving output signals from each of said sensor units of said first pair and circuit means for monitoring output signals from each of said sensor units of said second pair;

traversing said survey pig through said pipeline and monitoring said sensor units to determine when an output signal is received from a sensor unit, respectively;

comparing output signals from said first pair of sensor units to determine if said first pair of sensor units have passed a girth weld or some other magnetic anomaly associated with said pipeline; and monitoring output signals from said second pair of sensor units and comparing signals related to output signals produced by said first pair of sensor units with output signals from said second pair of sensor units to determine the velocity of said survey pig through said pipeline.

5. In a pipeline survey pig adapted to traverse a section of generally cylindrical fluid transmission pipeline made up of pipe sections which are welded end to end with generally transverse girth welds, said survey pig including support members for supporting said survey pig for traversal through said pipeline, a girth weld detection system characterized by:

a first pair of girth weld sensor units supported on said pig spaced apart circumferentially with respect to a central longitudinal axis of said pipeline and in relatively close proximity to an interior wall surface of said pipeline, said sensor units of said first pair each including means for generating a magnetic fluid field which is interruptible by a girth weld as said sensor units of said first pair pass said girth weld while said pig is traversing said pipe, said sensor units of said first pair each including means for generating an electrical sensor output signal in response to interruption of said magnetic flux field;

circuit means operably connected to said sensor units of said first pair for receiving said sensor output signals and for generating a signal related to said sensor units of said first pair sensing only a girth weld in said pipeline;

a second pair of sensor units supported on said pig circumferentially spaced apart one from the other and with respect to said axis, said second pair of sensor units being spaced axially from said first pair of sensor units;

circuit means associated with said second pair of sensor units for generating a signal in response to output signals from each sensor unit of said second pair when said second pair of sensor units passes said girth weld; and circuit means for timing the generation of signals related to said first pair of sensor units passing said girth weld and said second pair of sensor units passing said girth weld for determining the velocity of said pig in said pipeline.

* * * * *